(12) United States Patent
Yari et al.

(10) Patent No.: US 8,999,662 B2
(45) Date of Patent: Apr. 7, 2015

(54) METHOD FOR PRODUCING DRY REAGENT, DRY REAGENT, AND ANALYSIS TOOL USING SAME

(71) Applicant: ARKRAY, Inc., Kyoto (JP)

(72) Inventors: Yui Yari, Kyoto (JP); Toshihiro Imai, Kyoto (JP); Tsutomu Nakamura, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 13/743,792

(22) Filed: Jan. 17, 2013

(65) Prior Publication Data
US 2013/0189721 A1 Jul. 25, 2013

(30) Foreign Application Priority Data
Jan. 22, 2012 (JP) ................. 2012-010553

(51) Int. Cl.
*C12Q 1/32* (2006.01)
*G01N 21/59* (2006.01)
*C12Q 1/26* (2006.01)

(52) U.S. Cl.
CPC *G01N 21/59* (2013.01); *C12Q 1/26* (2013.01); *C12Q 1/32* (2013.01)

(58) Field of Classification Search
None
See application file for complete search history.

(56) References Cited

U.S. PATENT DOCUMENTS

| 4,547,460 | A | 10/1985 | Eikenberry |
| 4,803,159 | A | 2/1989 | Smith-Lewis |
| 2011/0104712 | A1 * | 5/2011 | Cubizolles et al. ............ 435/7.4 |
| 2013/0092536 | A1 * | 4/2013 | Carrington et al. ...... 204/403.04 |

FOREIGN PATENT DOCUMENTS

| EP | 0009222 A2 * | 4/1980 |
| EP | 0239990 A2 | 10/1987 |
| EP | 0272518 A2 | 6/1988 |
| JP | 1988-157998 A | 6/1988 |
| JP | 1993-060360 B | 9/1993 |
| JP | 1996-248028 A | 9/1996 |
| JP | 1998-197526 A | 7/1998 |
| JP | 2001204461 A * | 7/2001 |
| WO | 2009-090756 A1 | 7/2009 |
| WO | WO 2010120786 A1 * | 10/2010 |

OTHER PUBLICATIONS

Ash, M., and Ash, I. Sorbitol. Handbook of Green Chemicals 2nd Ed. 2008, Synapse Information Resources, Inc., pp. 2060-2061.*
Schiweck, H., Bar, A., Vogel, R., Schwarz, E., Kunz, M., Lussem, B., Moser, M., and Peters, S. Sugar Alcohols. Ullmann's Encyclopedia of Industrial Chemistry 2011, Wiley-VCH: Weinheim, Germany, pp. 6-11.*
Ko, J.-S., Oh, S.-W., Kim, K.-W., Nakashima, N., Nagadome, S., and Sugihara, G. "Blending effects on adsorption and micellization of different protein solubilizers: A thermodynamic study on three mixed systems of CHAPS with MEGA-8, -9 and -10 in pH 7.2 phosphate buffered solution", Colloids and Surfaces B: Biointerfaces 2005, vol. 45, pp. 90-103.*
Extended European Search Report issued in corresponding European Patent Application No. 13152237.7 dated Jun. 11, 2013.
Allain et al., "Rapid single-step kinetic colorimetric assay for lactate dehydrogenase in serum," Clinical Chemistry, 19: 223-227 (1973).

* cited by examiner

*Primary Examiner* — Allison Fox
*Assistant Examiner* — Michelle F Paguio Frising
(74) *Attorney, Agent, or Firm* — Morgan, Lewis & Bockius LLP

(57) ABSTRACT

Provided is a dry reagent that allows measuring with good precision, in accordance with a transmission method that utilizes light of the ultraviolet region, increases or decreases of a nicotinamide coenzyme, in order to quantify a component contained in a liquid sample.

A dry reagent 4 for performing a quantitative analysis of a specific component in a liquid sample S contains a nicotinamide coenzyme and a leveling agent for smoothing the dry reagent 4. Increases or decreases of the nicotinamide coenzyme are measured in accordance with a transmission method that utilizes light of the ultraviolet region. The leveling agent is a combination of an alkali and at least one type selected from among a saccharide and a surfactant.

13 Claims, 12 Drawing Sheets

FIG3.C

COMPARATIVE EXAMPLE 1: $\beta$-NAD+ ALONE

DRY REAGENT    CRACKS

COMPARATIVE EXAMPLE 1: β-NAD+ ALONE

COMPARATIVE EXAMPLE 2: β-NAD+ + NaOH

EXAMPLE 2: β-NAD+ + MEGA8(6W/V%)
+ NaOH

DRY REAGENT 4

EXAMPLE 5: β-NAD+ + SUCROSE(20W/V%)
+ NaOH

DRY REAGENT 4

COMPARATIVE EXAMPLE 3: β-NADH ALONE

EXAMPLE 7: β-NADH + SUCROSE (3W/V%)
+ CHAPS (0.1W/V%)

DRY REAGENT 4

METHOD FOR PRODUCING DRY REAGENT, DRY REAGENT, AND ANALYSIS TOOL USING SAME

BACKGROUND OF THE INVENTION

1. Field of the Invention

The present invention relates to a method for producing a dry reagent that is used in analysis of components that are contained in a liquid sample, and to a dry reagent and an analysis tool that uses the dry reagent.

2. Description of the Related Art

Nicotinamide coenzymes (for instance, β-NAD+, β-NADH, β-NADP+ and β-NADPH) are widely used as detection reagents among reagents for measuring, in accordance with enzymatic methods, the amount of components, for instance AST (aspartate aminotransferase) or LDH (lactate dehydrogenase) contained in a liquid sample. For instance, Japanese Unexamined Patent Application Publication No. H8-248028 discloses a liquid reagent that contains a nicotinamide coenzyme and that is used for measuring components in a liquid sample. In this liquid reagent, the increase or decrease of a nicotinamide coenzyme is measured in accordance with a transmission method that utilizes light of a wavelength (340 nm) in the ultraviolet region.

There have been proposed analysis tools for measuring, in a simpler manner, the amount of components in liquid sample, wherein the analysis tool is provided with a detection reagent in the form of a dry reagent that contains a nicotinamide coenzyme. For instance, Japanese Examined Patent Application Publication No. H5-60360 discloses an analysis tool wherein multiple gelatin layers are formed on a substrate, and β-NAD+, which is one nicotinamide coenzyme, is contained in the layers. The analysis tool does not detect directly β-NADH, which results from reduction of β-NAD+; instead, the analysis tool comprises a formazan dye precursor and an electron transfer agent, as a β-NADH detection agent. Specifically, diaphorase is used as the electron transfer agent and nitrotetrazolium blue (hereafter NTB) is used as the formazan dye precursor. The change in color of NTB is detected in accordance with a reflection method that utilizes light of a wavelength in the visible region.

WO 2009/090756 discloses an analysis tool that is made up of a sample supply port through which a liquid sample is supplied into the analysis tool, a measurement chamber in which the liquid sample is measured, and a flow channel that communicates the sample supply port with the measurement chamber. The flow channel and the measurement chamber are porous plate members that are formed through stacking of a plurality of plate members at least one of which has air permeability. Transport of the liquid sample in this analysis tool is accomplished not by capillarity, but, for instance, by pressure that is applied from the sample supply port. A dry reagent is disposed in the measurement chamber of the analysis tool. In this dry reagent as well, β-NAD+ is used as a detection reagent. Herein, β-NADH resulting from reduction of β-NAD+ is not detected directly; instead, the dry reagent comprises a β-NADH detection agent that detects β-NADH resulting from reduction of β-NAD+. Diaphorase is used as an electron transfer agent, and WST-4, which is a water-soluble tetrazolium salt, is used as a formazan dye precursor. The color change of WST-4 is detected in accordance with a transmission method that uses a wavelength in the visible region.

Japanese Unexamined Patent Application Publication No. H10-197526 discloses an analysis tool comprising a transparent substrate and a transparent cover, and an analyzer for measuring the analysis tool. In this analysis tool, a measurement chamber having a dry reagent disposed therein, and a capillary flow channel for transport of a liquid sample to the measurement chamber, are formed through bonding of the transparent substrate and the transparent cover to each other. The liquid sample that is transported in the measurement chamber dissolves the dry reagent. In the analyzer, a change in color that arises as a result of a reaction between the detection reagent that is contained in the dry reagent and a specific component in the liquid sample is measured in accordance with a transmission method that utilizes light of the visible region. Measurements in the analysis tool are performed with the liquid sample sealed. Contamination in the analyzer can be prevented accordingly. Therefore, the interior of the analyzer need not be cleaned. The analyzer is made smaller through improvements in an optical system. This dry reagent does not comprise a nicotinamide coenzyme as a detection reagent.

However, the above conventional technologies leave room for improvement as regards the features below.

Enzymatic methods that utilize nicotinamide coenzymes are widely used, as disclosed in Japanese Unexamined Patent Application Publication No. H8-248028, Japanese Examined Patent Application Publication No. H5-60360, and WO 2009/090756. However, lack of interchangeability in the measured values may preclude comparing patient data and may interfere with diagnosis. Therefore, the International Federation of Clinical Chemistry (IFCC) issues standard measurement methods (IFCC-recommended methods), at the international level, while the Japan Society of Clinical Chemistry (JSCC) publishes JSCC-recommended methods in Japan. A major characterizing feature of these recommended methods is that the amount of nicotinamide coenzymes are measured directly at 340 nm, which is a wavelength in the ultraviolet region. Such recommended methods are used in the liquid reagent disclosed in Japanese Unexamined Patent Application Publication No. H8-248028, but are also preferably used in analysis tools for easy measurement, such as those disclosed in Japanese Examined Patent Application Publication No. H5-60360 and WO 2009/090756.

However, measurements that rely on light of a wavelength (340 nm) in the ultraviolet region are fundamentally difficult to perform in reflection methods. Therefore, analysis tools that work on the basis of a reflection method such as the one disclosed in Japanese Examined Patent Application Publication No. H5-60360 rely necessarily on a measurement principle that utilizes light of a visible region, unlike the above-mentioned recommended methods.

In the analysis tools disclosed in WO 2009/090756 and Japanese Unexamined Patent Application Publication No. H10-197526, measurements are performed in accordance with a transmission method. In the analysis tools disclosed in WO 2009/090756 and Japanese Unexamined Patent Application Publication No. H10-197526, the amount of nicotinamide coenzymes are not directly measured at a wavelength in the ultraviolet region, as described above. In the analysis tool disclosed in WO 2009/090756, transport of the liquid sample is performed through application of pressure from a sample supply port. Analyzers for measuring such analysis tools are provided with a pump or the like for transporting a liquid sample, and hence tend to be large in size. In terms of achieving a smaller analyzer, it is preferable to use an analysis tool where a liquid sample is transported by capillarity, as in the analysis tool disclosed in Japanese Unexamined Patent Application Publication No. H10-197526.

In the analysis tool disclosed in Japanese Unexamined Patent Application Publication No. H10-197526, measurements relying on visible light are performed using a dry reagent that is disposed in a measurement chamber. In such an analysis tool, the dry reagent must be uniformly dissolved in the measurement chamber in order to perform measurements with good precision in accordance with the abovementioned recommended methods, in particular in accordance with a transmission method that utilizes ultraviolet light. Therefore, the dry reagent that is disposed in the measurement chamber must be smooth and free of cracks. However, it has been found that simple drying of reagent solutions in which nicotinamide coenzymes are dissolved result in impaired smoothness and formation of cracks. Unevenness arises in such dry reagents when dissolved without agitation, and hence achieving a target absorbance is difficult in cases where measurements are performed using light of the ultraviolet region. Moreover, cracks in the dry reagent result in bubbles that get caught in the cracks when a liquid sample flows into the measurement chamber. Bubbles present in such photometric sections are one cause of error in measured values.

SUMMARY OF THE INVENTION

It is a problem of the present invention, which was arrived at in the light of the above considerations, to provide a method for producing a dry reagent, and a dry reagent, that allow measuring, with good precision, increases or decreases of a nicotinamide coenzyme, in accordance with a transmission method that utilizes light of the ultraviolet region, in order to quantify a component contained in a liquid sample, and to provide an analysis tool that uses the dry reagent.

In order to solve the above problem, the present invention relies on the following technical means.

A method for producing a dry reagent provided according to a first aspect of the present invention is a method for producing a dry reagent for performing a quantitative analysis of a specific component that is contained in a liquid sample, the method comprising the steps of: adjusting a reagent solution by dissolving, in a dissolving solution, a nicotinamide coenzyme an increase or decrease whereof is measured in accordance with a transmission method that utilizes light of the ultraviolet region, and a leveling agent for smoothing the dry reagent; and dripping a predetermined amount of the reagent solution onto a substrate or a cover of an analysis tool, followed by drying.

Preferably, the leveling agent is a combination of an alkali and at least one type selected from among a saccharide and a surfactant. The term "saccharide" according to the present invention is meant by a concept including monosaccharide, oligosaccharide such as disaccharide, and sugar alcohol.

Preferably, the saccharide is sucrose, and in the step of adjusting the reagent solution, the concentration of sucrose in the reagent solution is adjusted to be 6 W/V % or more.

Preferably, the surfactant is at least one type selected from among n-octanoyl-N-methyl-D-glucamine and 3-[(3-cholamidopropyl)dimethylammonio]-1-propanesulfonate, and in the step of adjusting the reagent solution, the concentration of n-octanoyl-N-methyl-D-glucamine in the reagent solution is adjusted to be 2 W/V % or more.

Preferably, the leveling agent contains the saccharide and the surfactant; the saccharide is at least one type selected from among D-sorbitol and sucrose, and in the step of adjusting the reagent solution, the concentration of D-sorbitol in the reagent solution is adjusted to be 6 W/V % or more and the concentration of sucrose is adjusted to be 3 W/V % or more; the surfactant is at least one type selected from among n-octanoyl-N-methyl-D-glucamine and 3-[(3-cholamidopropyl) dimethylammonio]-1-propanesulfonate, and in the step of adjusting the reagent solution, the concentration of n-octanoyl-N-methyl-D-glucamine in the reagent solution is adjusted to be 3 W/V % or more, and the concentration of 3-[(3-cholamidopropyl)dimethylammonio]-1-propanesulfonate in the reagent solution is adjusted to be 0.1 W/V % or more.

A dry reagent provided according to a second aspect of the present invention is a dry reagent for performing a quantitative analysis of a specific component that is contained in a liquid sample, comprising: a nicotinamide coenzyme; and a leveling agent for smoothing the dry reagent, wherein an increase or decrease of the nicotinamide coenzyme is measured in accordance with a transmission method that utilizes light of the ultraviolet region.

Preferably, the leveling agent is a combination of an alkali and at least one type selected from among a saccharide and a surfactant.

Preferably, the alkali is sodium hydroxide.

Preferably, the saccharide is at least one compound selected from among D-sorbitol and sucrose.

Preferably, the surfactant is at least one type selected from among n-octanoyl-N-methyl-D-glucamine and 3-[(3-cholamidopropyl)dimethylammonio]-1-propanesulfonate.

Preferably, the dry reagent is accommodated in the interior of an analysis tool; the analysis tool includes a measurement chamber that transmits the light of the ultraviolet region, and the dry reagent is disposed in the measurement chamber.

Preferably, the analysis tool includes a capillary flow channel for transporting the liquid sample to the measurement chamber by capillarity; and the dry reagent is dissolved, without agitation, by the liquid sample that is transported by the capillary flow channel.

An analysis tool provided according to a third aspect of the present invention is an analysis tool for performing a quantitative analysis of a specific component that is contained in a liquid sample, wherein the dry reagent provided according to the second aspect of the present invention is accommodated in the interior of the analysis tool.

Preferably, a measurement chamber is provided in the interior of the analysis tool; the measurement chamber is a portion that transmits the light of the ultraviolet region, in order to measure an increase or decrease of the nicotinamide coenzyme, and the dry reagent is disposed in the measurement chamber.

Preferably, the analysis tool includes a capillary flow channel for transporting the liquid sample to the measurement chamber by capillarity, and the dry reagent is dissolved, without agitation, by the liquid sample that is transported by the capillary flow channel.

Other features and advantages of the present invention will become more apparent from the description of embodiments of the invention set forth below with reference to accompanying drawings.

DESCRIPTION OF THE PREFERRED EMBODIMENTS

Preferred embodiments of the present invention are specifically explained next with reference to accompanying drawings.

Figure 1:
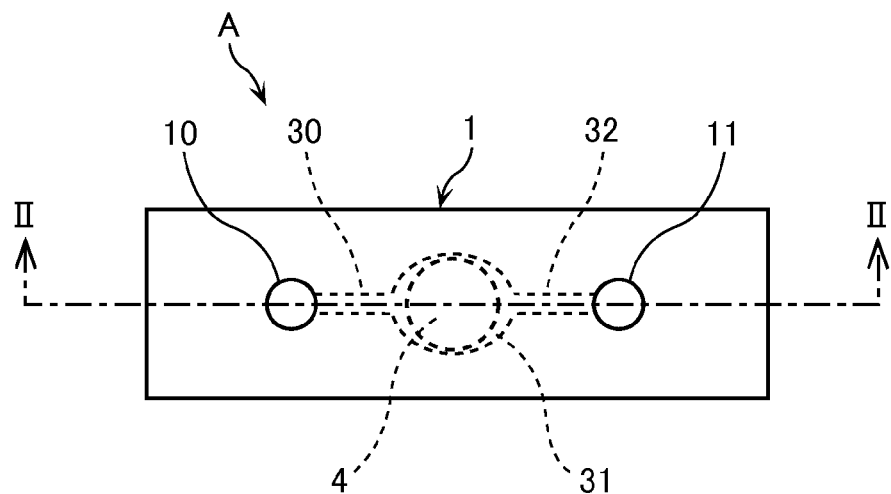
FIG. 1 is a plan-view diagram illustrating an example of an analysis tool provided with a dry reagent according to the present invention.
Figure 2:
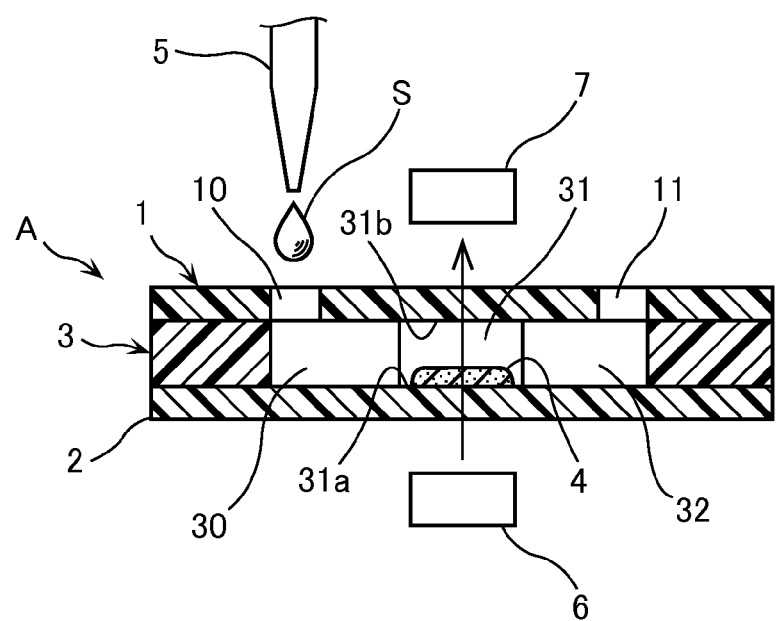
FIG. 2 is a cross-sectional diagram, along line II-II, of the analysis tool illustrated in FIG. 1.

FIG. 1 and FIG. 2 illustrate examples of a dry reagent in which the present invention is used, and of an analysis tool that comprises the dry reagent. An analysis tool A is set in a small analyzer that is installed in clinics or hospital wards, and that is used for quantitative analysis of the amount of components contained in serum. Serum corresponds herein to one example of the liquid sample in the present invention. The analysis tool A can be used in liquid samples other than serum. Specific examples of liquid samples other than serum include, for instance, biological samples such as whole blood, plasma, urine, saliva, interstitial fluid and the like. These liquid samples may be used as-is, or diluted in a diluting solution. As illustrated in FIG. 1 and FIG. 2, an analysis tool A comprises a cover 1, a substrate 2, a spacer 3, capillary flow channels 30, 32, a measurement chamber 31 and a dry reagent 4. In the explanation below, directions such as the vertical direction and so forth conform to directions as depicted in the drawings.

The cover 1 is a transparent plate-like member, made for instance of poly(methyl methacrylate) (PMMA), having ultraviolet transparency. The thickness of the plate-like member is 0.1 mm. Any member can be used as the cover 1 so long as the member is a plate-like member having ultraviolet transparency. Specific examples of materials of the plate-like member include, for instance, polyethylene terephthalate (PET). The thickness is not limited to 0.1 mm. Specifically, for instance, the thickness ranges preferably from 0.1 mm to 1.0 mm, and more preferably from 0.1 mm to 0.2 mm. A sample supply port 10 and a vent 11 are formed in the cover 1. As illustrated in FIG. 2, the sample supply port 10 is an opening for enabling a nozzle 5, which is provided in the analyzer, to supply serum S to the analysis tool A. The vent 11 is an opening that is formed for the purpose of enabling serum S in the interior of the analysis tool A to be transported smoothly by capillarity.

Like the cover 1, the substrate 2 is a transparent plate-like member of a material such as PMMA or the like having ultraviolet transparency. The thickness of the plate-like member is 0.1 mm. Any member can be used as the substrate 2 so long as the member is a plate-like member having ultraviolet transparency. Specific examples include, for instance, a plate-like member having PET as a material. The thickness is not limited to 0.1 mm. Specifically, for instance, the thickness ranges preferably from 0.1 mm to 1.0 mm, and more preferably from 0.1 mm to 0.2 mm. As illustrated in FIG. 1 and FIG. 2, the dry reagent 4 is formed and disposed at a portion, in the substrate 2, that constitutes a bottom wall section of the below-described measurement chamber 31.

As illustrated in FIG. 1 and FIG. 2, a spacer 3 is a member for bonding the cover 1 and the substrate 2 together, and for forming the capillary flow channels 30, 32 and the measurement chamber 31 in the interior of the analysis tool A. For instance, a 0.5 mm-thick double-sided tape is used as the spacer 3. The thickness of the spacer determines the cell length of the measurement chamber. The double-sided tape is a member resulting from coating both sides of a synthetic resin-made film with an adhesive. Through-holes that are shaped as the below-described capillary flow channels 30, 32 and the measurement chamber 31 are formed in the spacer 3, the capillary flow channels 30, 32 and the measurement chamber 31 being formed through bonding of the cover 1 and the substrate 2 by the spacer 3. The thickness of the spacer 3 is not limited to 0.5 mm. In cases where the analysis tool A is used for measuring the amount of a component that is contained in a large amount in the serum S, the thickness of the spacer 3 may be reduced to adjust thereby the sensitivity to a lower sensitivity. Conversely, when the analysis tool A is used for measuring components that are present in very small amounts in the serum S, the spacer 3 is made thicker, to increase sensitivity thereby.

As illustrated in FIG. 2, the capillary flow channel 30 is a flow channel for enabling serum S that is supplied through the sample supply port 10, out of the nozzle 5, to move, by capillarity, to the below-described measurement chamber 31. The capillary flow channel 32 is a channel for transporting serum S from the measurement chamber 31 to the vent 11. The capillary flow channel 32 is provided for the purpose of reliably filling the measurement chamber 31 with the serum S.

As illustrated in FIG. 1 and FIG. 2, the measurement chamber 31 is a small space, formed in the interior of the analysis tool A, that is surrounded by a top wall section, a side wall section and a bottom wall section. The measurement chamber 31 is a chamber for holding the below-described dry reagent 4. As illustrated in FIG. 2, the dry reagent 4 is fixed to a bottom wall face 31a of the measurement chamber 31. The serum S flows into the measurement chamber 31 through the capillary flow channel 30. The inflowing serum S dissolves the dry reagent 4. The dissolved reagent diffuses in the measurement chamber 31. The dissolved reagent and the serum S are not agitated herein. The dry reagent 4 can be fixed to a top wall face 31b of the measurement chamber 31. In the case of a reagent that is unstable when separated from other reactions, a plurality of dry reagents 4 that contain these reagents separated from each other can be disposed by being fixed to both the top wall face 31b and the bottom wall face 31a.

As illustrated in FIG. 1 and FIG. 2, the top wall sections of the capillary flow channels 30, 32 and of the measurement chamber 31 are formed by the cover 1. The side wall section is formed by the spacer 3. The bottom wall section is formed by the substrate 2. The surface of the cover 1 and the substrate 2 is subjected to a physical treatment, for instance, ultraviolet treatment or plasma treatment, in order for capillarity to be reliably elicited. The surface treatment of the cover 1 and the substrate 2 is not limited to a physical treatment, and may involve coating with a surfactant.

The dry reagent 4 is obtained by mixing a plurality of reagents that detect specific components contained in the serum S, and by drying the resulting mixture. The dry reagent 4 contains a nicotinamide coenzyme as a detection reagent. Nicotinamide coenzymes are coenzymes required in reactions that are catalyzed by certain oxidoreductases. Specific examples of nicotinamide coenzymes include, for instance, β-nicotinamide adenine dinucleotide (β-NAD+), reduced β-nicotinamide adenine dinucleotide (β-NADH), β-nicotinamide adenine dinucleotide phosphate (β-NADP+) and reduced β-nicotinamide adenine dinucleotide phosphate (β-NADPH). Herein, β-NAD+ and β-NADH are interconverted as a result of reactions catalyzed by oxidoreductases. Likewise, β-NADP+ and β-NADPH undergo interconversion. From among the foregoing, β-NADH and (β-NADPH, which are reduced nicotinamide coenzymes, have an absorption maximum in the vicinity of 340 nm. In a detection system where a nicotinamide coenzyme is required, therefore, the analyzer quantifies specific components that are contained in the serum S through detection of the increase or decrease of β-NADH or β-NADPH.

Examples components that can be detected by a detection system in which nicotinamide coenzymes are involved include, for instance, substances such as glucose, uric acid, triglycerides, ammonia, creatinine, and enzymes such as creatine kinase, transaminase, leucine aminopeptidase, α-amylase, lactate dehydrogenase.

For instance, lactate dehydrogenase (LDH) catalyzes a reaction in which pyruvic acid is generated from lactic acid. In that reaction, β-NAD+ is reduced to β-NADH. As described above, β-NAD+ and β-NADH exhibit significantly dissimilar absorption spectra at wavelengths in the ultraviolet region. Herein, β-NAD+ exhibits absorption only in the vicinity of 260 nm, and β-NADH exhibits absorption also in the vicinity of 340 nm. Therefore, the activity of LDH can be detected by measuring the increase in the absorbance of β-NADH at 340 nm.

[Chem. 1]

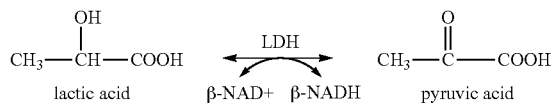

The dry reagent 4 contains a leveling agent. The purpose of the leveling agent is to smooth out the shape of the dry reagent 4 and prevent cracks. As described above, the dry reagent 4 is disposed in the measurement chamber 31 of the analyzer A. The dry reagent 4 is dissolved by the serum S in the measurement chamber 31 without agitation. The measurement is performed through irradiation of ultraviolet light into the dissolving solution of the dry reagent 4. The dissolving solution is not agitated, and hence the reagent concentration in the dissolving solution exhibits unevenness readily when irregularities are present in the surface of the dry reagent 4. Also, bubbles are likely to occur in the dissolving solution when cracks are present in the dry reagent 4. Variability in the measurement data occurs readily as a result. Therefore, the surface of the dry reagent 4 must be smooth. A leveling agent is used to that end in the dry reagent 4. The leveling agent is a combination of an alkali and at least one type selected from among a saccharide and a surfactant. The term "saccharide" according to the present invention is meant by a concept including monosaccharide, oligosaccharide such as disaccharide, and sugar alcohol. The saccharide may be used singly or concomitantly in the form of two or more types. The same is true of the surfactant. The saccharide and the surfactant may be used concomitantly. The alkali is, specifically, sodium hydroxide (NaOH). Specific examples of the saccharide include, for instance, glycerin, D-sorbitol, sucrose and trehalose. Specific examples of the surfactant include, for instance, n-octanoyl-N-methyl-D-glucamine (MEGA8) and 3-[(3-cholamidopropyl)dimethylammonio]-1-propanesulfonate (CHAPS). Herein, MEGA8 is particularly appropriate for smoothing a dry reagent 4 that contains β-NAD+, while CHAPS is particularly appropriate for smoothing a dry reagent 4 that contains β-NADH.

In the leveling agent, an aqueous solution of NaOH can be used as a reagent dissolving solution. In this case, the concentration of NaOH ranges preferably from 0.5 N to 1.5 N, and is more preferably adjusted to 1.0 N.

If sucrose is used singly as the saccharide, the concentration thereof is preferably adjusted to 6 W/V % or more. In a case where CHAPS is used as the surfactant, the concentration thereof is preferably set to 2 W/V % or more.

If the saccharide and the surfactant are used concomitantly, the foregoing are preferably used having had the concentration thereof adjusted as follows. In a case where, for instance, D-sorbitol is used as the saccharide, the concentration thereof is preferably adjusted to 6 W/V % or more. If sucrose is used, the concentration thereof is preferably set to 3 W/V % or more. If MEGA8 is used as the surfactant, the concentration thereof is preferably adjusted to 3 W/V % or more. If CHAPS is used, the concentration thereof is preferably set to 0.1 W/V % or more.

These leveling agents function as so-called excipients or binders. The binding ability between powder particles in low-molecular powders such as β-NAD+ and β-NADH is low, since such powders have little bound water. When a reagent obtained by mixing such components is dried, fine cracks appear on the surface of the dry reagent. Cracks appear also on account of light impacts. The reason for such occurrences is deemed to stem from the fact that in the drying process, powder molecules that dry off more readily cover the surface of the reagent solution, so that the properties of the powder keep being renewed thereby. In the case of a dry reagent 4 having such a component blended thereinto, cracking can be improved through dispersion and further hydration of the powder.

In a case where, for instance, there is added a saccharide that comprises bound water, for instance sucrose or trehalose, or a polyol such as glycerin or D-sorbitol, these saccharides are dried, while the powder molecules are being dispersed, in the drying process of the dry reagent 4. Saccharide molecules bound in the drying process form a matrix into which powder molecules such as β-NAD+ and β-NADH are taken up. The properties of the saccharide, the molecules whereof readily bind to each other, are preserved thereby. It is deemed that cracking in the dry reagent 4 improves as a result. It is likewise found that a surfactant such as MEGA8 or CHAPS contributes to improving cracking through a similar action.

The analysis tool A is produced as follows. Firstly, the reagent solution is adjusted by dissolving the nicotinamide coenzyme and the leveling agent in the dissolving solution. Specific examples of the dissolving solution include, for instance, pure water, buffer solutions and the like. Next, a predetermined amount of the reagent solution is spotted at a portion of the substrate 2 that constitutes the measurement chamber 31, and the dry reagent 4 is formed then through drying under predetermined conditions (FIG. 1 and FIG. 2). Next, a double-sided tape, as the spacer 3, is affixed to the top of the substrate 2, to secure cell length, and the cover 1, of the same material as that of the substrate 2, is bonded to the spacer 3. The analysis tool A is produced as a result (FIG. 1 and FIG.

2). Nicotinamide coenzymes that are more appropriate for the detection system are selected herein. The leveling agent is selected as described above. Through-holes shaped as the capillary flow channels 30, 32 and the measurement chamber 31 are formed in the spacer 3. Spotting of the reagent solution may involve, firstly, affixing of the spacer 3 to the substrate 2, followed by spotting on the portion of the substrate 2 that corresponds to the measurement chamber 31. The sample supply port 10 and the vent 11 are formed in the cover 1.

The operation of the analysis tool A that comprises the dry reagent 4 according to the present invention will be explained next with reference to FIG. 2 and FIG. 3A to FIG. 3C.

Measurement that utilizes the analysis tool A is performed in accordance with a transmission method using light of a wavelength in the ultraviolet region. As illustrated in FIG. 2, light of the ultraviolet region is irradiated, as indicated by the arrow, towards the measurement chamber 31 in which the dry reagent 4 is disposed. The light source element 6 becomes disposed below the measurement chamber 31 upon setting of the analysis tool A in the analyzer. The purpose of the light source element 6 is to irradiate light of a wavelength in the vicinity of 340 nm to the measurement chamber 31. The light of the ultraviolet region that is irradiated by the light source element 6 may be any light, provided that it enables detecting increases or decreases of the nicotinamide coenzyme, but is preferably selected in a range from 200 nm to 400 nm. A light-receiving element 7 of the analyzer is disposed above the measurement chamber 31. The purpose of the light-receiving element 7 is to receive light that passes through the measurement chamber 31.

Figure 3A:
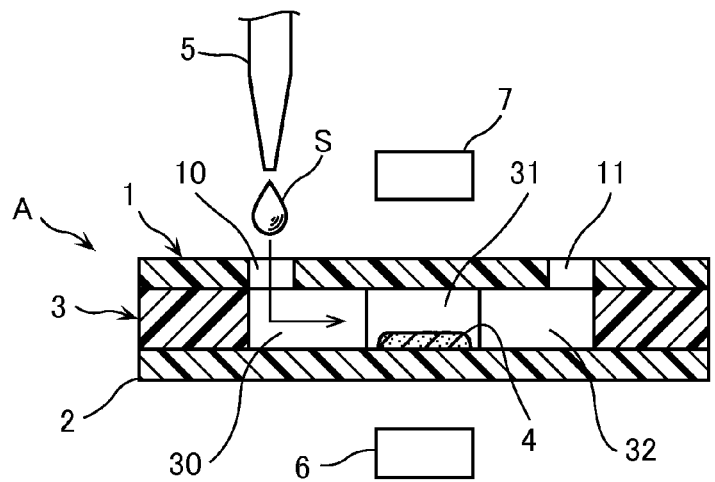
FIG. 3 is a set of cross-sectional diagrams FIG. 3A to FIG. 3C for explaining the operation of the analysis tool illustrated in FIG. 1.
Figure 3B:
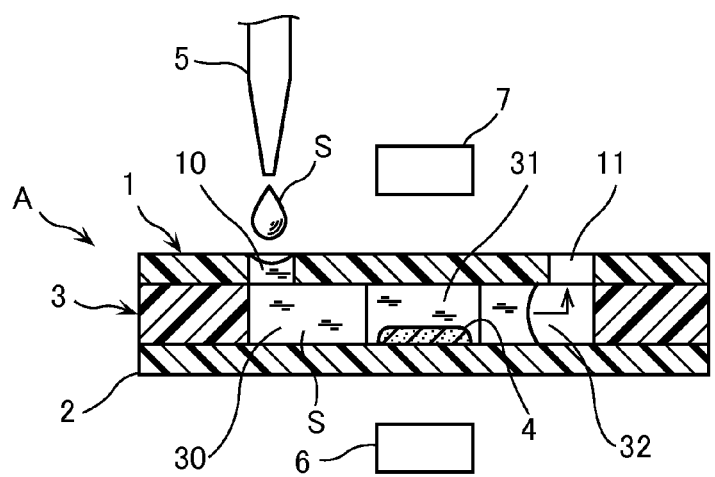
Figure 3B:
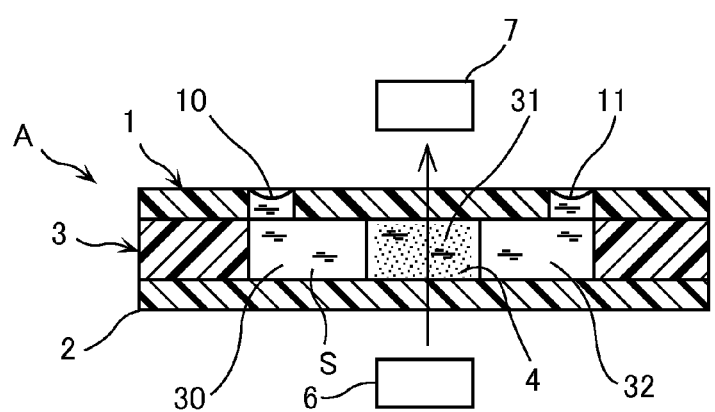

As illustrated in FIG. 3A, a nozzle 5 of the analyzer supplies the serum S into the analysis tool A via the sample supply port 10. On account of capillarity, the serum S moves through the capillary flow channel 30 as indicated by the arrow, towards the measurement chamber 31. Next, the serum S flows into the measurement chamber 31, as illustrated in FIG. 3B. The serum S fills the measurement chamber 31, and moves thereafter through the capillary flow channel 32, as indicated by the arrow. Next, serum S in an amount sufficient for filling the interior of the analysis tool A is caused to flow from the nozzle 5 into the sample supply port 10. Next, as illustrated in FIG. 3C, the serum S dissolves the dry reagent 4 that is disposed in the measurement chamber 31. Dissolution of the dry reagent 4 by the serum S is accomplished without agitation. Next, the light source element 6 irradiates ultraviolet light of a wavelength in the vicinity of 340 nm into the measurement chamber 31, as indicated by the arrow. This light passes through the reagent dissolving solution in the measurement chamber 31, and is received by the light-receiving element 7. The analyzer calculates the amount of a specific component in the serum S on the basis of the amount of light received in the light-receiving element 7. The dry reagent comprises a nicotinamide coenzyme, and hence quantitative analysis of the specific component contained in the serum S is accomplished through detection of the increase or decrease of β-NADH or β-NADPH.

In the present embodiment, as described above, the dry reagent 4 that is accommodated in the analysis tool A contains a leveling agent for smoothing the dry reagent 4. As a result, the dry reagent 4 is a smooth dry reagent, with few cracks or irregularities. Bubbles and concentration unevenness of the reagent 4 do not occur thus readily when the dry reagent 4 is dissolved by the serum S. Therefore, analysis results of good precision can be obtained, when performing a quantitative analysis of a specific component contained in the serum S, by measuring the amount of nicotinamide coenzyme in accordance with a transmission method that utilizes light of the ultraviolet region. Accordingly, measurements that utilize an IFCC-recommended method or JSCC-recommended method can be performed in the analysis tool A for easy measurement.

The leveling agent contained in the dry reagent 4 is a combination of an alkali and at least one type selected from among a saccharide and a surfactant. The leveling agent allows forming appropriately a dry reagent having a smooth flat surface. As a result, analysis results of good precision can be obtained when performing a quantitative analysis of a specific component contained in the serum S.

In the analysis tool A, the dry reagent 4 is disposed in the measurement chamber 31 into which ultraviolet light is irradiated. Therefore, no reagent dissolved in the serum S need be transported. Measurements can be performed with good precision, since there arises no reagent concentration unevenness due to transport.

The analysis tool A is provided with the capillary flow channel 30 for transport of the serum S to the measurement chamber 31 by capillarity, such that the dry reagent 4 can be dissolved, without agitation, by the serum S that is transported by the capillary flow channel 30. Accordingly, the analyzer for measuring the analysis tool A need not be provided with parts such as a pump or the like for transporting the serum S. Also, it is not necessary to provide an agitation device for agitating the dissolving solution of the reagent in the measurement chamber 31. Accordingly, the analysis tool A and the abovementioned analyzer can be made smaller, and the manufacturing costs of the forming can be kept low.

The present invention is not limited to the features of the above-described embodiments. The specific features of the steps in the method for producing a dry reagent according to the present invention can be modified in various ways. Likewise, the specific configuration of the dry reagent and analysis tool according to the present invention may accommodate numerous design variations.

EXAMPLES

The effect of the present embodiment is explained specifically below on the basis of examples and comparative examples. The present invention is not limited to any of these examples.

There was prepared a dry reagent 4 illustrated in FIG. 1 and FIG. 2 of the present embodiment and an analysis tool A that comprised the dry reagent 4. Firstly, there was adjusted a reagent solution for forming the dry reagent 4.

Example 1

Herein, 13.27 mg of β-NAD+ (by Oriental Yeast) were added to 0.234 mL of pure water, and were completely dissolved, followed by addition of 0.016 mL of 1N—NaOH (by Wako Pure Chemical Industries), with agitation, to prepare a first solution. Further, 13.27 mg of β-NAD+ and 15.0 mg of surfactant MEGA8 (by Dojindo Laboratories) were added to 0.234 mL of pure water and were completely dissolved, followed by addition of 0.016 mL of 1N—NaOH, with agitation, to prepare a second solution. A reagent solution was then adjusted by mixing 20 μL of the first solution and 10 μL of the second solution. In this case, the concentration of MEGA8 in the reagent solution is 2 W/V %.

Example 2

The second solution of Example 1 was used, without modification, as the reagent solution. In this case, the concentration of MEGA8 in the reagent solution is 6 W/V %.

Example 3

Herein, 13.27 mg of β-NAD+ were added to 0.234 mL of pure water and were completely dissolved, followed by addition of 0.016 mL of 1N—NaOH, with agitation, to prepare a first solution. Further, 13.27 mg of β-NAD+ and 50.0 mg of sucrose (by Nacalai Tesque) were added to 0.234 mL of pure water, and were completely dissolved, followed by addition of 0.016 mL of 1N—NaOH, with agitation, to prepare a second solution. A reagent solution was then adjusted by mixing 21 μL of the first solution and 9 μL of the second solution. In this case, the concentration of sucrose in the reagent solution is 6 W/V %.

Example 4

A reagent solution was then adjusted by mixing 15 μL of the first solution and 15 μL of the second solution of Example 3. In this case, the concentration of sucrose in the reagent solution is 10 W/V %.

Example 5

The second solution of Example 3 was used, without modification, as the reagent solution. In this case, the concentration of sucrose in the reagent solution is 20 W/V %.

Example 6

Herein, 13.27 mg of β-NAD+ and 15.0 mg of D-sorbitol (by Nacalai Tesque), and 7.5 mg of MEGA8 were added to 0.234 mL of pure water, and were completely dissolved, followed by addition of 0.016 mL of 1N—NaOH, with agitation, to prepare a reagent solution. In this case, the concentration of D-sorbitol in the reagent solution is 6 W/V %, and the concentration of MEGA8 is 3 W/V %.

Comparative Example 1

Herein, 13.27 mg of β-NAD+ were dissolved in 0.25 mL of pure water, to prepare a reagent solution. The reagent solution differs from that of the dry reagent 4 of the present embodiment, in that the reagent solution comprises no NaOH, surfactant or saccharide.

Comparative Example 2

Herein, 13.27 mg of β-NAD+ were added to 0.234 mL of pure water and were completely dissolved, followed by addition of 0.016 mL of 1N—NaOH, with agitation, to prepare a reagent solution. The reagent solution differs from that of the dry reagent 4 of the present embodiment, in that the reagent solution comprises no surfactant or saccharide.

Next, dry reagents 4 were formed using the above reagent solutions, to prepare analysis tools A. Dry reagents and analysis tools were produced in the same way for Comparative example 1 and Comparative example 2. Each reagent solution was spotted at the portion, of the PMMA substrate 2, corresponding to the measurement chamber 31. The whole was placed in a low-humidity vault (trade mark: McDry, by ERC), and was dried overnight under conditions of room temperature and 1% RH, to form the respective dry reagent 4. Next, a 0.488 mm-thick double-sided tape, as the spacer 3, was affixed to the top of the substrate 2, to secure cell length, and a cover 1 of the same material as that of the substrate 2 was affixed thereon, to produce a respective analysis tool A as a result. The measurement chamber 31 of the analysis tool A is configured to have a photometric section diameter of 2.5 mm, a cell length of 0.488 mm and a volume of 2.39 μL.

Figure 4:
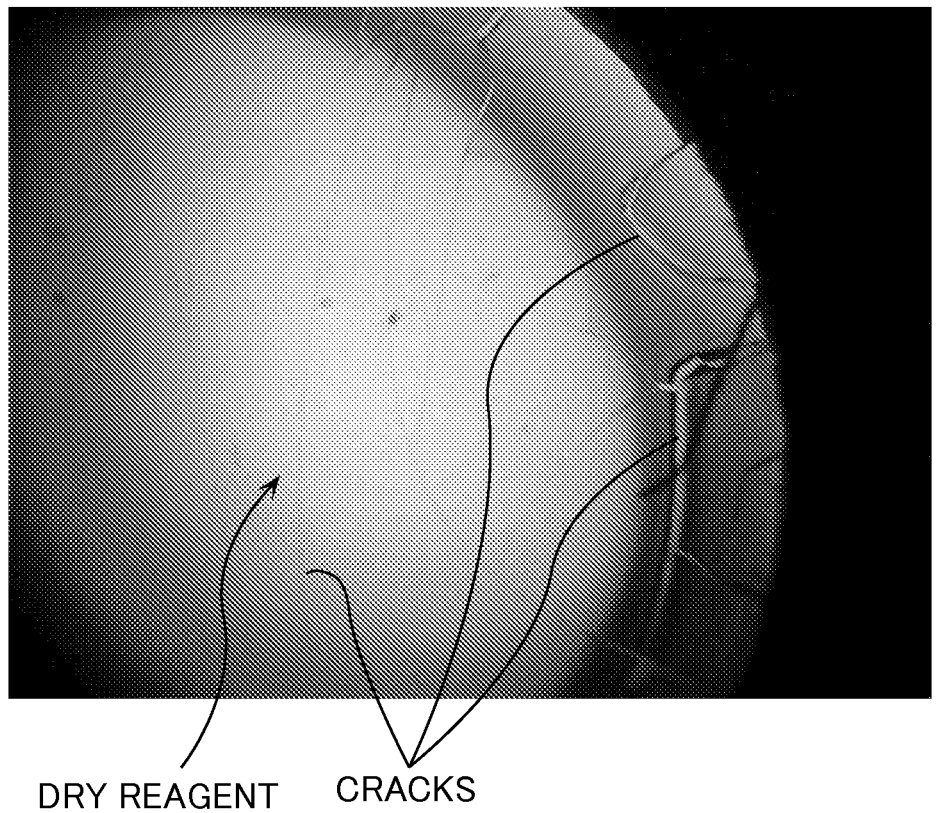
FIG. 4 is a photograph illustrating a surface state of a dry reagent of Comparative example 1.
Figure 5:
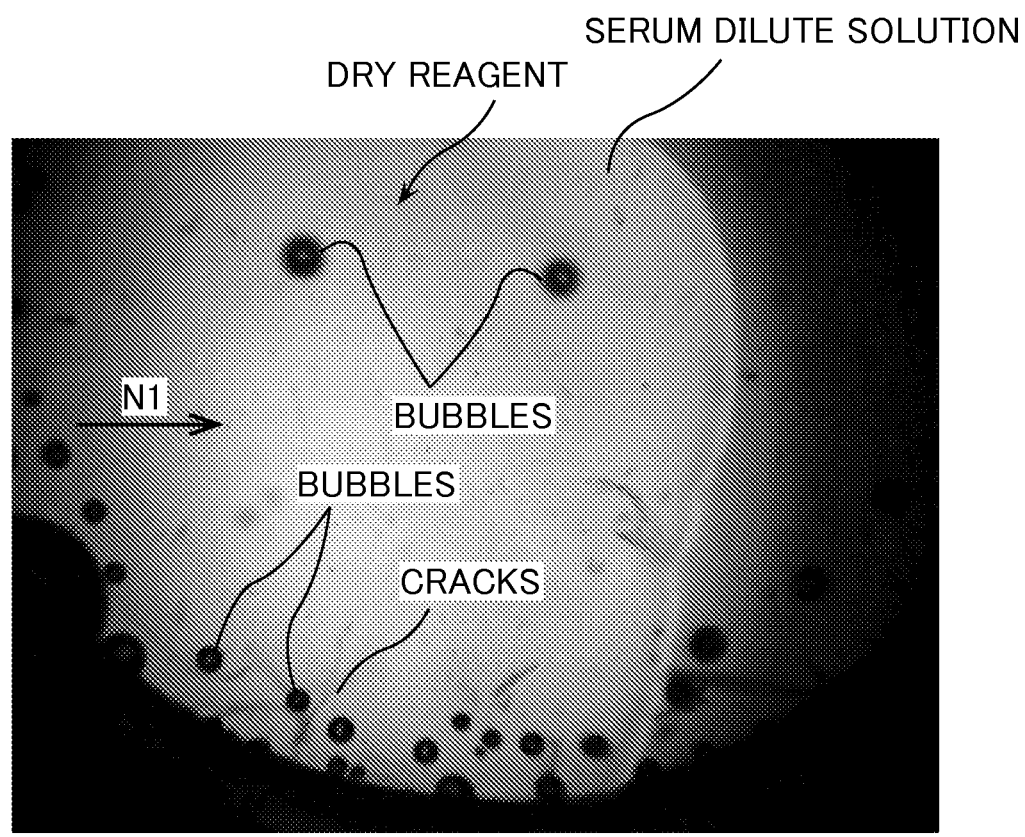
FIG. 5 is a photograph illustrating a state in which a liquid sample is transported over the dry reagent of Comparative example 1.
Figure 6:
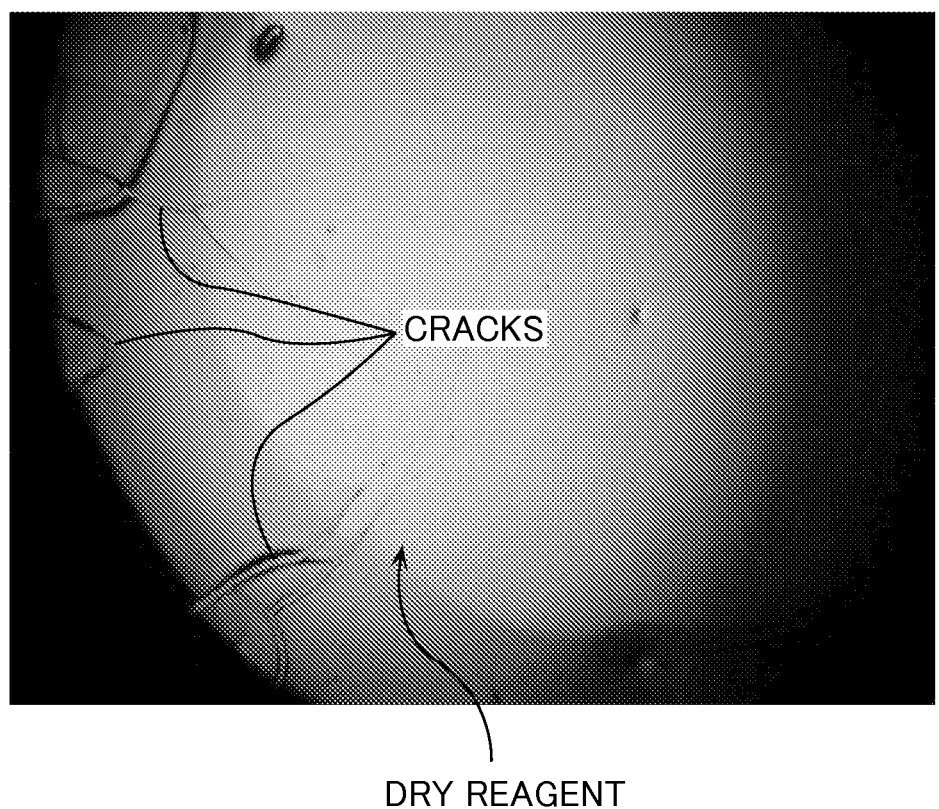
FIG. 6 is a photograph illustrating a surface state of a dry reagent of Comparative example 2.

FIG. 4 to FIG. 6 illustrate the surface state of the dry reagents that are produced in Comparative example 1 and Comparative example 2. FIG. 4 illustrates the surface state of a dry reagent of β-NAD+ alone. Cracks form on the surface of the dry reagent. Although not readily apparent from FIG. 4, the overall shape of the dry reagent is that of a doughnut, with a recessed central portion. FIG. 5 illustrates a state upon supply of a serum dilute solution, resulting from mixing human serum with a below-described LDH reaction system R1 reagent, to a dry reagent of β-NAD+ alone. Bubbles are formed, by residual air in cracks, when the serum dilute solution flows into the measurement chamber 31 of the analysis tool, as indicated by arrow N1. FIG. 6 illustrates the surface state of the dry reagent of Comparative example 2. The dry reagent differs from that of Comparative example 1 in that the dry reagent contains NaOH in addition to β-NAD+. Herein as well, as in the case of Comparative example 1, cracks appear on the surface of the dry reagent.

Figure 7:
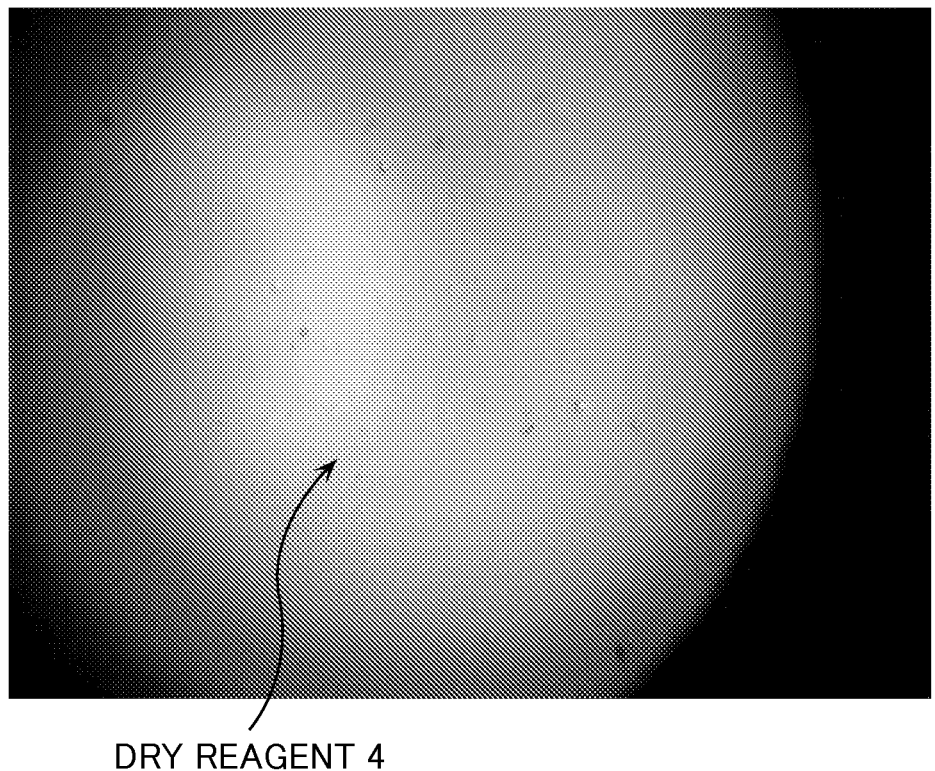
FIG. 7 is a photograph illustrating a surface state of a dry reagent of Example 2.
Figure 8:
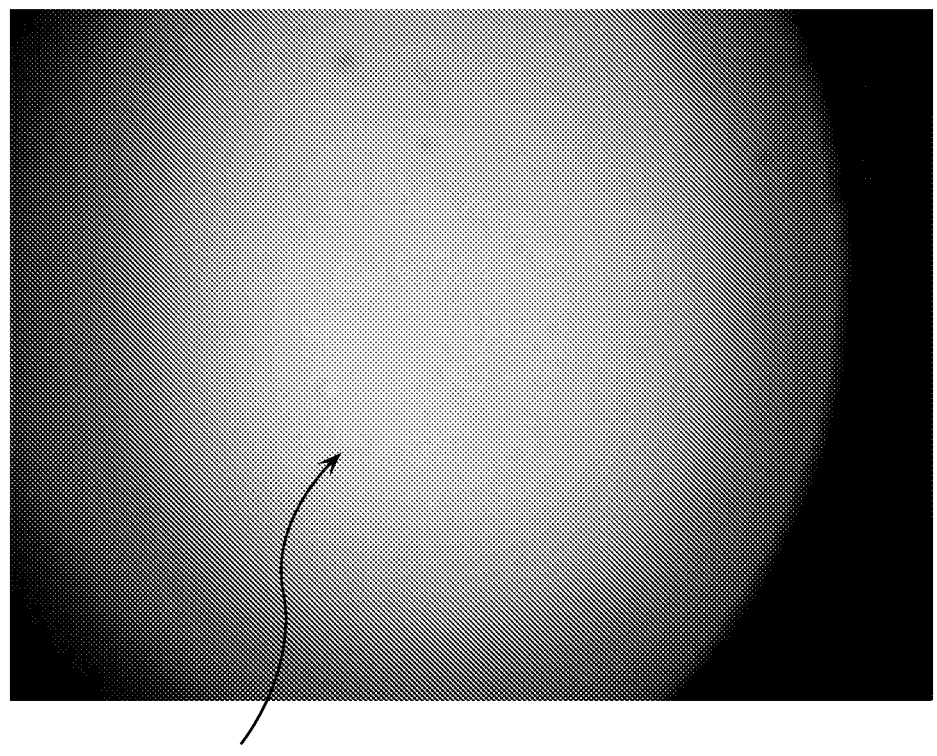
FIG. 8 is a photograph illustrating a surface state of a dry reagent of Example 5.

FIG. 7 and FIG. 8 illustrate the surface state of dry reagents 4 that are produced in Example 2 and Example 5. FIG. 7 illustrates the surface state of the dry reagent 4 of Example 2. The dry reagent 4 contains MEGA8, which is a surfactant, in addition to NaOH. The reagent solution for forming the dry reagent 4 comprises 6 W/V % of MEGA8. The surface of the dry reagent 4 is smooth, without cracks. FIG. 8 illustrates the surface state of the dry reagent 4 of Example 5. The dry reagent 4 contains sucrose in addition to NaOH. The reagent solution for forming the dry reagent 4 comprises 20 W/V % of sucrose. The surface of the dry reagent 4, like that of the dry reagent 4 of Example 2, is smooth, without cracks.

The analysis tools A are evaluated using an LDH reaction system R1 reagent. The purpose of the LDH reaction system R1 reagent is to supply lactic acid, which is the substrate of lactate dehydrogenase (LDH) that is present in serum. The dry reagent 4 should contain lactic acid if the purpose of the analysis tool A is to measure LDH. However, for convenience in the evaluation, a LDH reaction system R1 reagent was prepared that contained lactic acid, and the LDH reaction system R1 reagent was mixed with human serum to yield a serum dilute solution. The method for adjusting of the LDH reaction system R1 reagent was as follows.

Herein, 31.09 g of 2-[n-cyclohexylamino]ethane sulfonic acid (CHES) (by Dojindo Laboratories) were dissolved in pure water at room temperature, and the pH was adjusted thereafter to 9.4 using a sodium hydroxide aqueous solution, to yield 100 mL of solution (hereafter, CHES buffer solution). As a surfactant solution, 25 mg of sodium deoxycholate (by Wako Pure Chemical Industries) were dissolved in pure water, to prepare 5 mL of a sodium deoxycholate aqueous solution. Then, 38.4 mg of lithium lactate (by Wako Pure Chemical Industries) were dissolved in 0.7 mL of pure water, and 0.2 mL of the CHES buffer solution and 0.1 mL of the sodium deoxycholate aqueous solution were added thereto, with agitation, to prepare the LDH reaction system R1 reagent.

Then, 5 μL of the above-described serum dilute solution (mixed solution of the LDH reaction system R1 reagent and human serum) were supplied to the sample supply port 10 of each produced analysis tool A. The reaction was left to proceed for 3 minutes at 37° C. As a result, β-NAD+ was reduced to β-NADH, and hence a time course measurement of the absorbance increment was performed at the 340 nm wavelength using a spectrophotometer. The measurement of the analysis tools of Comparative example 1 and Comparative example 2 was performed in the same way.

Figure 9:
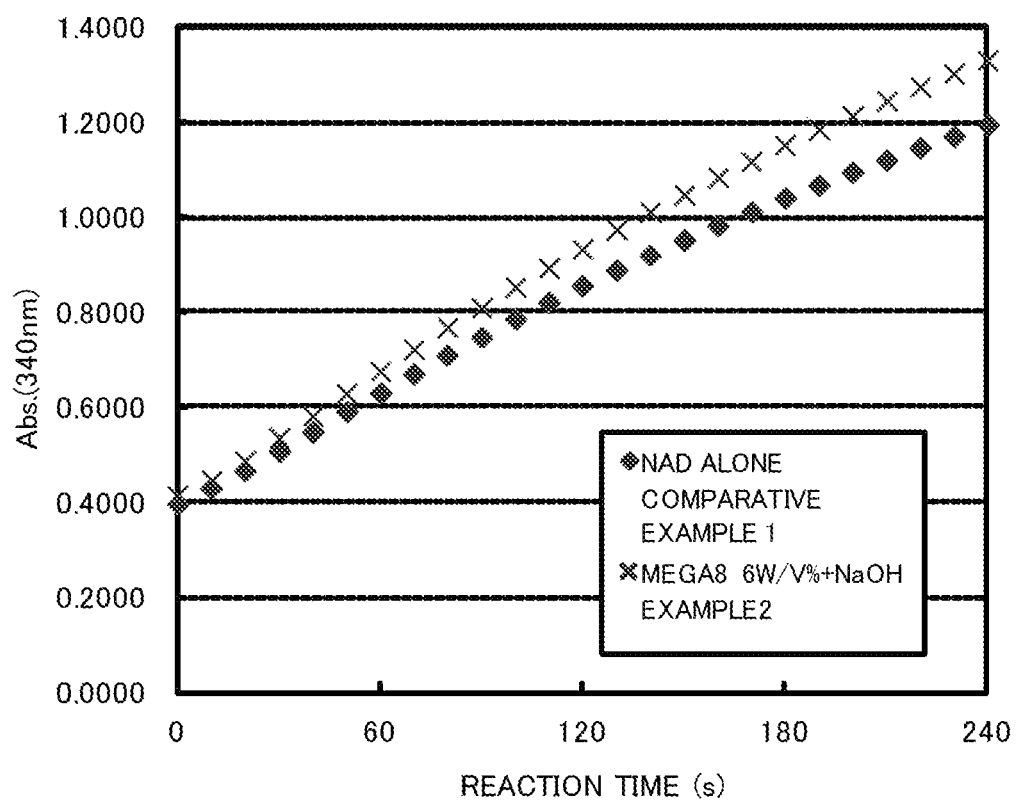
FIG. 9 is a graph of a comparison of the time course of absorbance in Comparative example 1 and Example 2.
Figure 10:
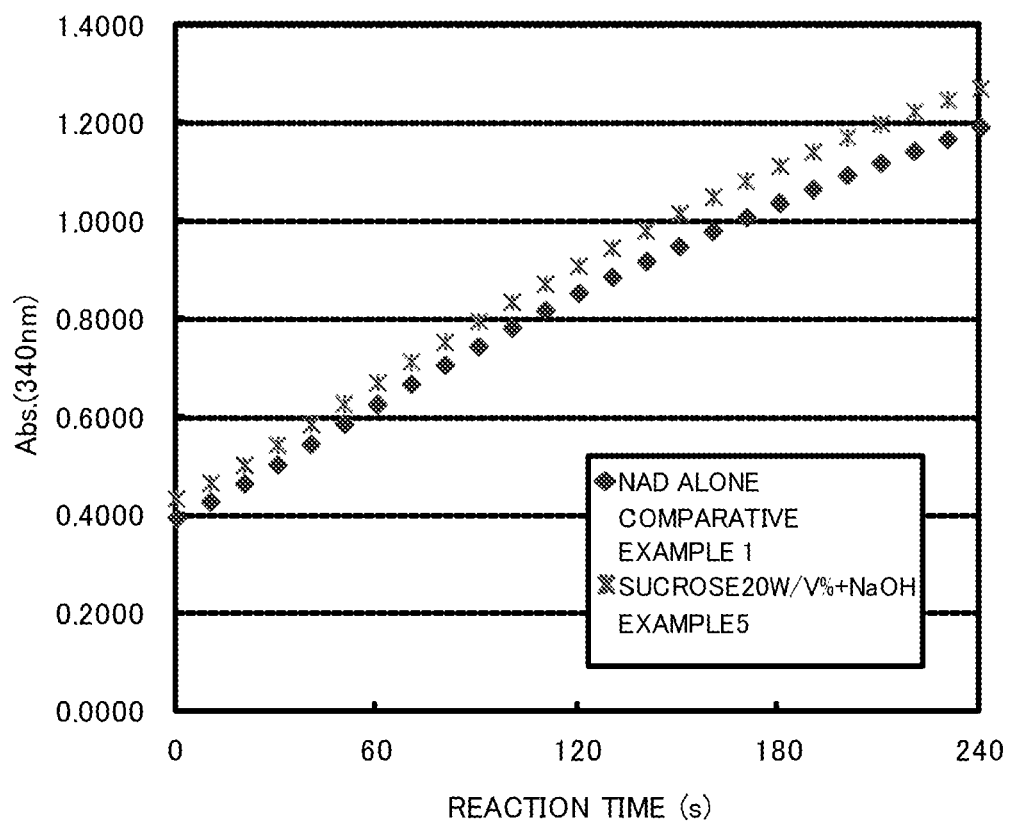
FIG. 10 is a graph of a comparison of the time course of absorbance in Comparative example 1 and Example 5.
Figure 11:
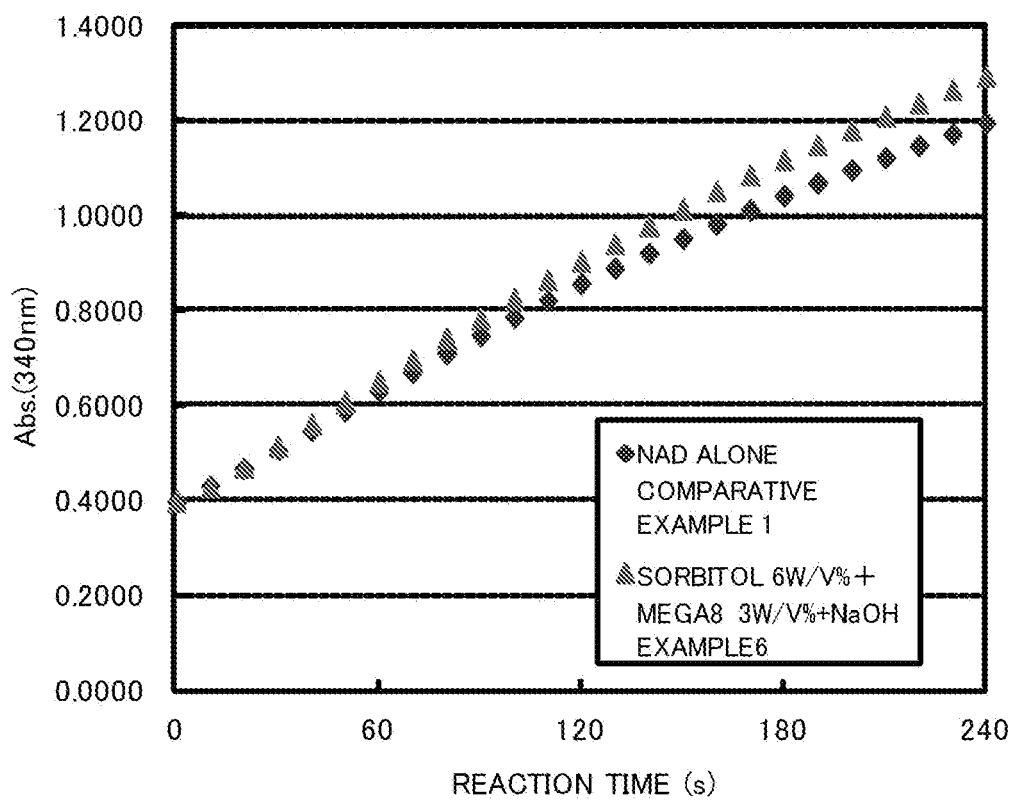
FIG. 11 is a graph of a comparison of the time course of absorbance in Comparative example 1 and Example 6.

FIG. 9 to FIG. 11 illustrate time courses upon supply of the above-described serum dilute solution to the analysis tool of Comparative example 1, and the analysis tools A of Example 2, Example 5 and Example 6. FIG. 9 illustrates a comparison between the time courses of Comparative example 1 and Example 2. The absorbance increment is greater for the dry reagent 4 that contains MEGA8 than for the dry reagent having β-NAD+ alone. The dry reagent of Comparative example 1 is dried to a doughnut shape, such that the reagent concentration in the dissolving solution becomes lower towards the central portion. In the analysis tool of Comparative example 1, the reagent dissolving solution in which the dry reagent is dissolved is not agitated, and hence absorbance at the portion of low reagent concentration is lower.

FIG. 10 illustrates a comparison between the time courses of Comparative example 1 and Example 5. The absorbance increment is greater for the dry reagent 4 that contains sucrose than for the dry reagent having β-NAD+ alone, for the same reasons as in Example 2. FIG. 11 illustrates a comparison between the time courses of Comparative example 1 and Example 6. The absorbance increment is greater for the dry reagent 4 that contains NaOH as well as MEGA8 and D-sorbitol, than for the dry reagent having β-NAD+ alone, for the same reasons as in Example 2. Effects are elicited at lower concentrations when combining a surfactant and a saccharide than in cases where the surfactant or the saccharide is added singly.

Table 1 sets out the variability (CV value: %) in absorbance after 70 seconds and after 80 seconds, for n=10 measurements each, using the analysis tools A of Example 1 to Example 6 and the analysis tools of Comparative example 1 and Comparative example 2. As described above, the dry reagents 4 of Example 1 and Example 2 contain NaOH and MEGA8. The dry reagents 4 of Example 3 to Example 5 contain NaOH and sucrose. The dry reagent 4 of Example 6 contains NaOH, D-sorbitol and MEGA8. As Table 1 shows, the variability of absorbance is small in a case where the dry reagent 4 comprises at least one from among NaOH, a surfactant and a saccharide. That is because the surface of the dry reagent 4 is smooth, and hence bubble formation is prevented, and it is likewise prevented that the reagent concentration in the dissolving solution should become nonuniform. Herein, the CV value (coefficient of variation) is an index of the variability of numerical values, and is obtained by multiplying by 100 the quotient of a standard deviation by a mean value.

water, followed by addition of 0.013 mL of the Tris-HCl buffer solution, with agitation, to prepare a reagent solution. In this case, the concentration of sucrose in the reagent solution is 3 W/V %, and the CHAPS concentration is 0.1 W/V %. The present example differs from Example 1 to Example 6 in that herein β-NADH is used, instead of β-NAD+, as the nicotinamide coenzyme.

Comparative Example 3

Herein, 1.06 mg of β-NADH were dissolved in 0.25 mL of pure water, to prepare a reagent solution. The present comparative example differs from Comparative example 1 and Comparative example 2 in that herein β-NADH is used, instead of β-NAD+, as the nicotinamide coenzyme.

Each reagent solution was spotted, in an amount of 2.39 μL, at the portion, of the substrate 2, corresponding to the measurement chamber 31. The whole was placed in a low-humidity vault, and was dried overnight under conditions of room temperature and 1% RH, to form a respective dry reagent 4. Next, a 0.488 mm-thick double-sided tape was affixed to the top of the substrate 2, to secure cell length, and a cover 1 of the same material as that of the substrate 2 was affixed thereon, to produce as a result an analysis tool A of Example 7. The measurement chamber of the analysis tool A is configured to have a photometric section diameter of 2.5 mm, a cell length of 0.488 mm and a volume of 2.39 μL. A dry reagent and an analysis tool were produced in the same way for Comparative example 3.

Human serum in an amount of 5 μL was spotted on the sample supply port 10 of the analysis tool A of Example 7 produced as described above. The reaction was left to proceed for 5 minutes at 37° C. A time course measurement was performed at the 340 nm wavelength using a spectrophotometer. The measurement of the analysis tool of Comparative example 3 was performed in the same way as described above.

Figure 12:
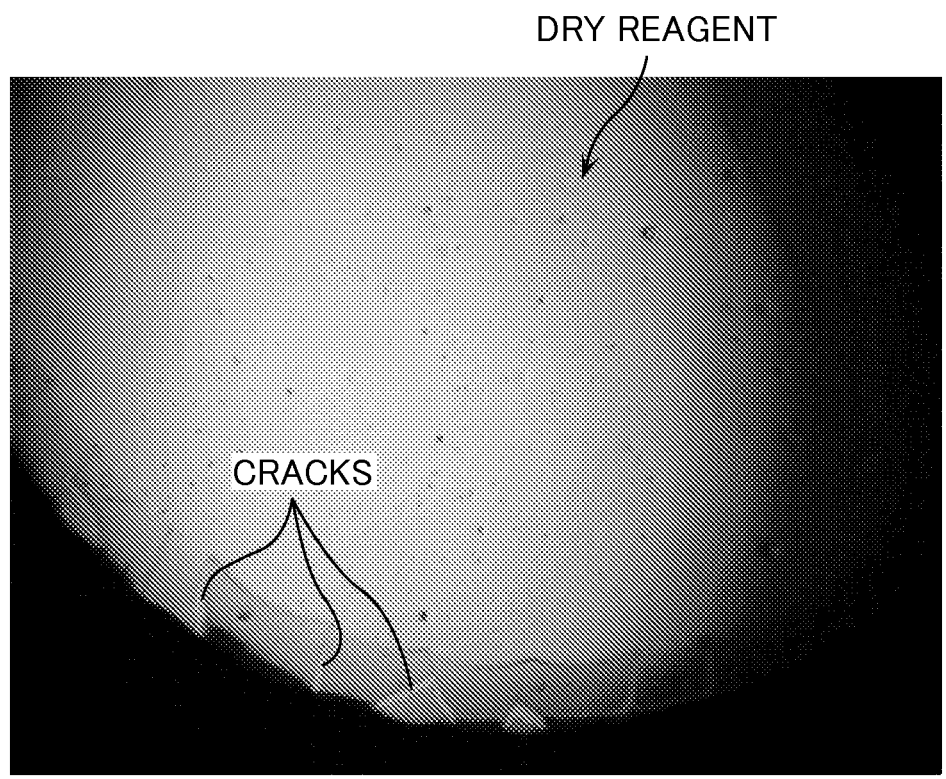
FIG. 12 is a photograph illustrating a surface state of a dry reagent of Comparative example 3.
Figure 13:
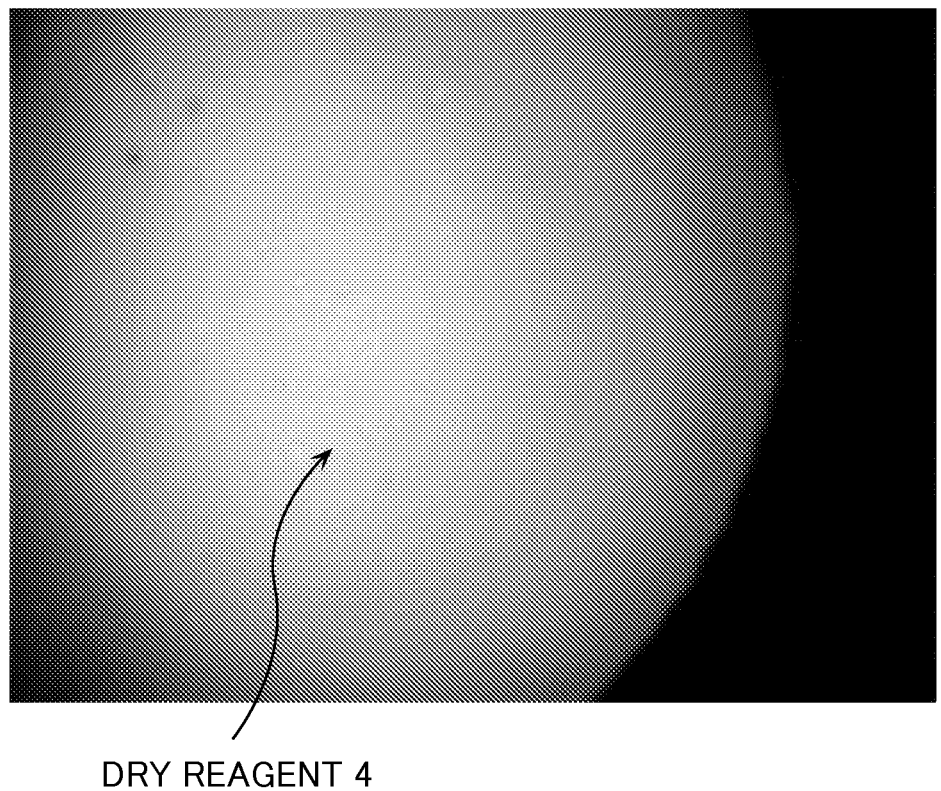
FIG. 13 is a photograph illustrating a surface state of a dry reagent of Example 7.

FIG. 12 illustrates a surface state of a dry reagent, containing β-NADH alone, that is produced in Comparative example 3. Cracks appear around the dry reagent. Although not readily apparent from FIG. 12, the overall shape of the dry reagent is that of a doughnut, with a recessed central portion. FIG. 13 illustrates the surface state of the dry reagent 4 produced in Example 7. The dry reagent 4 contains sucrose and CHAPS in addition to NaOH. As described above, the reagent solution

TABLE 1

| Time after reaction start (sec) | Comp. ex. 1 | Comp. ex. 2 | Example 1 | Example 2 | Example 3 | Example 4 | Example 5 | Example 6 |
|---|---|---|---|---|---|---|---|---|
| 70 | 4.6% | 4.7% | 1.5% | 3.2% | 2.1% | 2.4% | 1.7% | 1.8% |
| 80 | 4.1% | 4.4% | 1.7% | 3.8% | 1.2% | 1.9% | 1.6% | 1.7% |

(CV value: %)

Example 7

Herein, 6.057 g of tris(hydroxymethyl)aminomethane (by Nacalai Tesque) were dissolved in pure water, and thereafter the pH was adjusted to pH 7.5 with hydrochloric acid (by Nacalai Tesque), to yield a 50 mL solution (hereafter, Tris-HCl buffer solution). Further, 1.06 mg of β-NADH (by Oriental Yeast), 7.5 mg of sucrose (by Nacalai Tesque) as a saccharide, and 0.25 mg of 3-[(3-cholamidopropyl)dimethylammonio]-1-propanesulfonate (CHAPS) (by Dojindo Laboratories), as a surfactant, were dissolved in 0.238 mL of pure for forming the dry reagent 4 comprises 3 W/V % of sucrose and 0.1 W/V % of CHAPS. Therefore, the surface of the dry reagent 4 is smooth, without cracks.

Table 2 sets out the variability (CV value: %) in absorbance after 120 seconds and after 143 seconds, for n=10 measurements each, using the analysis tool A of Example 7 and the analysis tool of Comparative example 3. As Table 2 shows, the variability of absorbance is smaller in the analysis tool A of Example 7 that comprises NaOH, sucrose and CHAPS, than in the analysis tool of Comparative example 3.

TABLE 2

| Time after reaction start (sec) | Comp. ex. 3 | Example 7 |
| --- | --- | --- |
| 120 | 26.7% | 8.1% |
| 143 | 24.7% | 9.0% |

(CV value: %)

What is claimed is:

1. A dry reagent for performing a quantitative analysis of a specific component that is contained in a liquid sample, comprising:
a nicotinamide coenzyme; and
a leveling agent for smoothing the dry reagent,
wherein an increase or decrease in the nicotinamide coenzyme is measured in accordance with a transmission method that utilizes light of the ultraviolet region,
wherein the leveling agent is a combination of an alkali and a surfactant,
wherein the dry reagent is disposed in a measurement chamber of an analysis tool, where the measurement chamber transmits the light of the ultraviolet region, and
wherein the surfactant is at least one selected from the group consisting of n-octanoyl-N-methyl-D-glucamine and 3-[(3-cholamidopropyl)dimethylammonio]-1-propanesulfonate.

2. The dry reagent according to claim 1, wherein the alkali is sodium hydroxide.

3. The dry reagent according to claim 1, wherein the analysis tool further comprises a capillary flow channel for transporting the sample to the measurement chamber.

4. The dry reagent according to claim 1, wherein the surfactant is 3-[(3-cholamidopropyl)dimethylammonio]-1-propanesulfonate.

5. The dry reagent according to claim 4, further comprising n-octanoyl-N-methyl-D-glucamine as the surfactant.

6. The dry reagent according to claim 1, wherein the leveling agent further comprises a saccharide, wherein the saccharide is at least one selected from the group consisting of D-sorbitol and sucrose.

7. An analysis tool for performing a quantitative analysis of a specific component that is contained in a liquid sample, wherein the dry reagent according to claim 1 is accommodated in the interior of the analysis tool.

8. The analysis tool according to claim 7,
wherein a measurement chamber is provided in the interior of the analysis tool;
said measurement chamber is a portion that transmits said light of the ultraviolet region, in order to measure an increase or decrease of said nicotinamide coenzyme, and said dry reagent is disposed in said measurement chamber.

9. The analysis tool according to claim 8,
wherein said analysis tool includes a capillary flow channel for transporting said liquid sample to said measurement chamber by capillarity, and said dry reagent is dissolved, without agitation, by said liquid sample that is transported by said capillary flow channel.

10. The method for producing the dry reagent according to claim 1, the method comprising the steps of:
adjusting a reagent solution by dissolving, in a dissolving solution, the nicotinamide coenzyme, and the leveling agent; and
dripping a predetermined amount of the reagent solution onto a substrate or a cover of an analysis tool, followed by drying.

11. The method for producing the dry reagent according to claim 10, wherein the leveling agent further comprises a saccharide, wherein the saccharide is sucrose, and in the step of adjusting the reagent solution, the concentration of sucrose in the reagent solution is adjusted to be 6 W/V % or more.

12. The method for producing the dry reagent according to claim 10, wherein in the step of adjusting the reagent solution, the concentration of n-octanoyl-N-methyl-D-glucamine in the reagent solution is adjusted to be 2 W/V % or more.

13. The method for producing the dry reagent according to claim 10, wherein
the leveling agent further comprises a saccharide, wherein the saccharide is at least one type-selected from the group consisting of D-sorbitol and sucrose, and in the step of adjusting the reagent solution, the concentration of D-sorbitol in the reagent solution is adjusted to be 6 W/V % or more and the concentration of sucrose is adjusted to be 3 W/V % or more; and
in the step of adjusting said reagent solution, the concentration of n-octanoyl-N-methyl-D-glucamine in said reagent solution is adjusted to be 3 W/V % or more, and the concentration of 3-[(3-cholamidopropyl)dimethylammonio]-1-propanesulfonate in said reagent solution is adjusted to be 0.1 W/V % or more.

* * * * *